United States Patent [19]

Bonne et al.

[11] Patent Number: 4,749,573

[45] Date of Patent: Jun. 7, 1988

[54] **COSMETIC PREPARATIONS USEFUL FOR OPPOSING SKIN AGING CONTAINING AN EXTRACT OF THE FRUITS OF *SILYBUM MARIANUM***

[76] Inventors: Claude Bonne, 316 avenue d'Occitanie, 34000 Montpellier; Daniel Sincholle, 343 avenue de la Trémoulette, 34980 Saint-Clement, both of France

[21] Appl. No.: 15,226

[22] Filed: Feb. 17, 1987

[30] Foreign Application Priority Data

Feb. 24, 1986 [FR] France ................... 86 02889

[51] Int. Cl.$^4$ .................... A61K 35/78; A61K 31/34
[52] U.S. Cl. ................................ 424/195.1; 514/458
[58] Field of Search ............... 424/195.1, 63; 514/458

[56] References Cited

FOREIGN PATENT DOCUMENTS

| | | |
|---|---|---|
| 1923082 | 11/1970 | Fed. Rep. of Germany . |
| 2017789 | 10/1971 | Fed. Rep. of Germany . |
| 3225688 | 1/1984 | Fed. Rep. of Germany . |
| 1073137 | 6/1976 | Japan . |
| 7028857 | 7/1977 | Japan . |
| 0822824 | 4/1981 | U.S.S.R. . |

*Primary Examiner*—Nicky Chan
*Assistant Examiner*—Wendy Davis
*Attorney, Agent, or Firm*—Wegner & Bretschneider

[57] ABSTRACT

The invention relates to novel cosmetic compositions containing an extract of the fruits of *Silybum marianum*. These compositions oppose aging of the skin.

7 Claims, No Drawings

COSMETIC PREPARATIONS USEFUL FOR OPPOSING SKIN AGING CONTAINING AN EXTRACT OF THE FRUITS OF *SILYBUM MARIANUM*

The present invention relates to a novel cosmetic composition opposing ageing of the skin.

The present invention relates in particular to a cosmetic composition containing as active principle an extract of the fruits of *Silybum marianum*.

The extract of the fruits of *Silybum marianum* L. (Gaertn.) or *Carduus marianum* L. is a mixture rich in flavonolignans which contains among others silybin, silydianin, silandrin, silychristin, silymonin, silybinomers resulting from the polymerization of silybine, these components being stabilized in the extract by various polyphenols such as taxifolol and other components such as dehydrodiconiferylic alcohol.

The extract of the fruits of *Silybum marianum* can be obtained by extraction of the fruits from which the lipids have been removed, with a solvent such as methanol, ethanol or acetone, as described by Wagner et al., Arzneim. Forsch. 1: 8, 688, 1968. The removal of the lipids may be obtained by using apolar solvents such as carbon tetrachloride or petroleum ether.

The plant and its active principles are known for their ability to protect the liver and have been used for this purpose in medicine since ancient times.

The applicants have discovered that the extract of the fruits of *Silybum marianum* have a radical-inhibiting activity and that topical compositions containing from 0.01 to 1% and especially 0.1 to 0.5% by weight of the extract of the fruits of *Silybum marianum* can oppose the degrading effects of free radicals which are partly responsible for aging of the skin.

Free radicals are normally produced in very small quantities during the life of a cell. They can be formed by the action of radiation in the UV as well as in the visible spectrum. The skin is particularly affected by this method of formation because of its direct exposure. However, free radicals are formed especially in physiological oxidation-reduction reactions. The radicals formed in this way are normally eliminated by enzyme systems which are capable of destroying them. When these systems are overloaded, however, as a result either or excessie radical formation or of defective detoxication mechanisms, the radicals react with the cell constituents and degrade them.

The cell constituents which represent the preferential targets for free radicals are of great functional importance. These constituents are primarily the polyunsaturated fatty acids forming part of the composition of the phospholipids which make up the cell membrane. When the radicals attack the fatty acids, disorganization spreads throughout the membrane and interferes with its functions, especially its role as a barrier in the epidermis, which ensures correct hydration of the skin.

Proteins, including enzyme proteins and structure proteins such as collagen and elastin—essential constituents of the dermis—are also a target for free radicals. Finally, nucleic acids, such as DNA—the carrier of the genetic code—are particularly sensitive to the denaturing action of free radicals. Their degradation, which, although minute, is continuous over the years, induces irreparable biochemical damage which is in part responsible for aging of the cell.

Through their radical-inhibiting activity, the extract of the fruits of *Silybum marianum* makes it possible to slow down aging of the skin.

The present invention consequently relates to a cosmetic composition opposing ageing of the skin which contains as active principle an extract of the fruits of *Silybum marianum*, at a dry extract concentration from 0.01 to 1% by weight and advantageously from 0.1 to 0.5% by weight.

The applicants have also discovered that the effect against the ageing of the skin may be increased by adding to the composition from 0.01 to 0.5% by weight of alpha-tocopherol. It should be noted that alpha-tocopherol is already present in the extract of the fruits of *Silybum marianum* but at a low concentration.

The following studies demonstrate the radical-inhibiting activity of the active principle used in the present invention.

The composition which was used in these studies was a solution, in polyethylene glycol 400, of the ethanol extract of the fruits of *Silybum marianum* from which the lipids had been removed, the dry extract content being 50 g/l. This solution is designated "SM Extract".

1. RADICAL-INHIBITING ACTIVITY TOWARDS THE SUPEROXIDE RADICAL ANION

The formation of the superoxide radical anion $(O_2^-)\cdot$ is a key step in the production of the other reactive species of oxygen and the subsequent organic radicals.

The superoxide radical is produced by a large number of oxidation-reduction reactions catalyzed by enzymes such as xanthine oxidase.

The protective effect of SM Extract is demonstrated in respect of the superoxide anion generated by this enzyme system in vitro, in the presence of cytochrome C, whose conversion is measured by spectrophotometry at 550 nm.

The results are given in Table I.

These results shown that SM Extract inhibits the conversion of cytochrome C by trapping the superoxide anion.

TABLE I

Radical-inhibiting activity measured according to the modified method described by CRAPO et al. 1978 (Methods in Enzymology, 53, 382–393)

| SM EXTRACT (mg/ml) | INHIBITION OF CYTOCHROME C CONVERSION (%) |
| --- | --- |
| 0 | 0 |
| 0.1 | 35 |
| 1 | 51 |
| 10 | 70 |

2. INHIBITION OF THE PEROXIDATION OF POLYUNSATURATED FATTY ACIDS (Bonne et al. 1985, Annals of Allergy 54, 158–160)

Blood platelets represent a very valuable model for studying the formation of free radicals and the products which are capable of trapping them in the cell environment. In fact, the platelets are particularly rich in enzymes which cause the peroxidation of unsaturated fatty acids. These reactions are initiated by the formation of radicals and can easily be measured by chromatographic separation of the metabolites formed from a $^{14}C$-labelled fatty acid such as arachidonic acid. The latter is metabolized mainly to thromboxane B2 (TxB2), hydroxyheptadecatrienoic acid+malonyldialdehyde (HHT+MDA) and hydroxy-12-eicosatetraenoic acid (12-HETE), the precursors of which are unstable peroxides. SM Extract inhibits the production of these metabolites by preventing the free-radical formation of the peroxides within the cells themselves, at SM Extract concentrations of between 0.10 and 0.25% (calculated as dry extract).

The results are given in Table II.

TABLE II

| SM EXTRACT (mg/ml) | Antiperoxidizing activity INHIBITION OF THE OXIDATIVE METABOLISM OF ARACHIDONIC ACID (%) |
| --- | --- |
| 0 | 0 |
| 5 | 3 |
| 10 | 9 |
| 15 | 25 |
| 20 | 44 |
| 25 | 63 |
| 50 | 100 |

3. INHIBITION OF THE FORMATION OF MALONYLDIALDEHYDE (MDA) IN THE SKIN

One of the signs of cell ageing which makes it possible to incriminate free radicals in the process of senescence is the accumulation of lipofuscins in the tissues. These pigments are Schiff's bases resulting from the reaction of primary amines with the malonyldialdehyde (MDA) produced by free-radical destruction of the lipids.

The protective effect as regards this process is demonstrated in the following test (Table III), in which, when diluted to 5% in a cosmetic excipient and applied to the skin of hairless mice, SM Extract inhibits the formation of MDA, induced by UV irradiation, in the skin tissue.

Hairless mice weighing 25-30 g are divided into groups of 5 animals and treated as indicated in the table. The intensity of the UV irradiation at 300 nm is 0.3 $J/cm^2$.

Nine hours after the irradiation is stopped, samples of dorsal skin are removed, weighed and homogenized in a buffered saline solution. The homogenate is centrifuged and the MDA is determined in the supernatant by spectrophotometry after reaction with thiobarbituric acid.

TABLE III

| | Protective activity in respect of the radicals induced by UV irradiation of the skin of hairless mice | |
| --- | --- | --- |
| GROUP | ANIMALS | FORMATION OF MDA (nmol/cm$^2$) |
| 1 | Non-irradiated control animals | 1 |
| 2 | Untreated irradiated animals | 60 |
| 3 | Irradiated animals treated with the excipient | 58 |
| 4 | Irradiated animals treated with SM Extract | 5 |

The cosmetic compositions according to the invention can also contain, if appropriate, any of the known substances which have beneficial properties on the skin, such as collagen, elastin, hyaluronic acid, lipids composed of unsaturated fatty acids, humectants, vitamin-enriched extracts, perfumes, preservatives and colorants. They can additionally contain solar radiation screens or filters.

The cosmetic compositions according to the invention can be presented in any of the forms used in cosmetology, i.e. as a cream or gel in jars or tubes, or as a milk or lotion in glass or plastic bottles and, if appropriate, in portioning bottles or alternatively ampoules.

The invention therefore relates in particular to cosmetic compositions which are in the form of a cream, gel, milk or lotion for the skin, and very particularly to cosmetic compositions whose excipients are adapted for application to the face and neck.

Each particular cosmetic form calls for appropriate excipients. These excipients must have all the properties which are normally demanded. Examples which may be mentioned are: glycerol stearate, propylene glycol, lanolin, glycerol, cetyl alcohol, polyols, vegetable, animal and mineral oils, waxes, wetting agents, and thickeners, stabilizers and emulsifiers which are in common use.

The various cosmetic forms mentioned above are obtained by the methods used in this field.

The present invention also relates to concentrated compositions intended for the manufacture of the cosmetic compositions according to the invention and containing from 1 to 10% by weight (as dry extract) of the extract of the fruits of Silybum marianum and advantageously also 0.2 to 2% by weight of alpha-tocopherol. Such compositions can be incorporated into bases appropriate for cosmetic compositions.

Examples of such compositions which may be mentioned are polyethylene glycol solutions of an alcohol extract of the fruits of Silybum marianum from which the lipides have been removed, such as the above mentioned SM Extract having a dry extract contents of 5% by weight. An other Example of such compositions is an extract designated "SMT Extract" comprising 5% by weight of extract of the fruits of Silybum marianum and 1% by weight of alpha-tocopherol in solution in polyethylene 400.

Examples of cosmetic compositions (in parts by weight) are now given below.

1. O/W cream

| | |
| --- | --- |
| Glycerol stearate | 5 |
| Wheatgerm oil | 10 |
| SM Extract or SMT Extract | from 2 to 10 |
| Propylene glycol | 3 |
| Carboxyvinylic polymer | 0.5 |
| Triethanolamine | 0.5 |
| Aromatic composition | q.s. |
| Preservatives | q.s. |
| Water | ad 100 |

2. O/W milk

| | |
| --- | --- |
| Oleyl alcohol polyethoxyetherphosphate | 2 |
| Cetyl alcohol | 0.5 |
| Anhydrous lanoline | 0.5 |
| Fluid silicone | 1 |
| Wheatgerm oil | 2 |
| Stearic acid | 3 |
| Triethanolamine | 0.5 |
| SM Extract or SMT Extract | from 2 to 6 |
| Magnesium aluminium silicate | 0.5 |
| Aromatic composition | q.s. |
| Preservatives | q.s. |
| Water | q.s. |

3. Aqueous-alcoholic lotion

| | |
| --- | --- |
| Cetyl alcohol | 0.5 |
| Stearic acid | 5 |
| Glycerol | 2 |
| SM Extract or SMT Extract | 3 |
| Na alginate | 0.3 |
| Triethanolamine | 0.5 |
| 94° alcohol | 5 |

| -continued | |
| --- | --- |
| Water | 83.7 |
| 4. Alcoholic hydrogel | |
| 40° alcohol | 95 |
| Triethylamine | 1.5 |
| EDTA | 0.05 |
| SM Extract or SMT Extract | 5 |
| Carbopol 940 | 1.5 |
| 5. Glycerized hydrogel | |
| Sodium alginate | 8 |
| Glycerol | 25 |
| Solution of borax (15%) in glycerol | 20 |
| SM Extract or SMT Extract | 5 |
| Thymol | 2 |
| Water | 45 |

What is claimed is:

1. A process for opposing ageing of the skin, which comprises applying to the skin a cosmetic composition containing from 0.01 to 1% by weight, calculated as dry extract, of an extract of the fruits of *Silybum marianum*, in an appropriate cosmetic base.

2. The process as claimed in claim 1, which comprises applying to the skin a cosmetic composition containing from 0.1 to 0.5% by weight, calculated as dry extract, of an extract of the fruits of *Silybum marianum*.

3. The process as claimed in claim 1, wherein the extract is an alcohol extract of the fruits of *Silybum marianum*.

4. The process as claimed in claim 2, wherein the extract is an alcohol extract of the fruits of *Silybum marianum*.

5. The process as claimed in claim 1, wherein the extract is a polyethylene glycol solution of an alcohol extract of the fruits of *Silybum marianum* from which the lipids have been removed.

6. The process as claimed in claim 2, wherein the extract is a polyethylene glycol solution of an alcohol extract of the fruits of *Silybum marianum* from which the lipids have been removed.

7. The process as claimed in any one of claims 1-6 which comprises applying to the skin a cosmetic composition containing in addition from 0.01 to 0.2% by weight of alpha-tocopherol.

* * * * *